(12) United States Patent
Folger et al.

(10) Patent No.: US 9,186,296 B2
(45) Date of Patent: *Nov. 17, 2015

(54) CONTAINERS FOR COMPOSITIONS COMPRISING MELOXICAM

(71) Applicant: Boehringer Ingelheim Vetmedica GmbH, Ingelheim am Rhein (DE)

(72) Inventors: Martin A. Folger, Ingelheim (DE); Samuel C. Crowley, Savannah, MO (US); Amy J. Wilson, Platte City, MO (US)

(73) Assignee: Boehringer Ingelheim Vetmedica GmbH, Ingelheim am Rhein (DE)

(*) Notice: Subject to any disclaimer, the term of this patent is extended or adjusted under 35 U.S.C. 154(b) by 206 days.

This patent is subject to a terminal disclaimer.

(21) Appl. No.: 13/799,901

(22) Filed: Mar. 13, 2013

(65) Prior Publication Data

US 2013/0161228 A1   Jun. 27, 2013

Related U.S. Application Data

(63) Continuation of application No. 12/901,649, filed on Oct. 11, 2010, now Pat. No. 9,101,529.

(60) Provisional application No. 61/250,709, filed on Oct. 12, 2009.

(51) Int. Cl.
| | |
|---|---|
| B65D 81/00 | (2006.01) |
| B65D 81/02 | (2006.01) |
| B65D 83/40 | (2006.01) |
| A61J 1/00 | (2006.01) |
| A61J 1/05 | (2006.01) |
| A61J 1/14 | (2006.01) |
| A61K 47/12 | (2006.01) |
| A61J 1/20 | (2006.01) |

(52) U.S. Cl.
CPC .... *A61J 1/00* (2013.01); *A61J 1/05* (2013.01); *A61J 1/1412* (2013.01); *A61J 1/2096* (2013.01); *A61K 47/12* (2013.01); *Y10T 428/1397* (2015.01)

(58) Field of Classification Search
CPC ............. A61J 1/00; A61J 1/05; A61J 1/1412; A61K 47/12
See application file for complete search history.

(56) References Cited

U.S. PATENT DOCUMENTS

| | | |
|---|---|---|
| 2,795,529 A | 6/1957 | Alburn et al. |
| 3,288,675 A | 11/1966 | Newmark et al. |
| 3,849,549 A | 11/1974 | Dempski et al. |
| 3,931,212 A | 1/1976 | Satzinger et al. |
| 3,947,576 A | 3/1976 | Kuczkowski et al. |
| 4,233,299 A | 11/1980 | Trummlitz et al. |
| 4,482,554 A | 11/1984 | Gebhardt et al. |
| 4,543,200 A | 9/1985 | Sherman |
| 4,628,053 A | 12/1986 | Fries |
| 4,748,174 A | 5/1988 | Veronesi |
| 4,794,117 A | 12/1988 | Corbiere |
| 4,802,926 A | 2/1989 | Kussendrager et al. |
| 4,835,187 A | 5/1989 | Reuter et al. |
| 4,942,167 A | 7/1990 | Chiesi et al. |
| 5,169,847 A | 12/1992 | Nagy nee Kricsfalussy et al. |
| 5,283,065 A | 2/1994 | Doyon et al. |
| 5,304,561 A | 4/1994 | Sarfarazi |
| 5,360,611 A | 11/1994 | Robertson et al. |
| 5,380,934 A | 1/1995 | Inoue et al. |
| 5,414,011 A | 5/1995 | Fu et al. |
| 5,654,003 A | 8/1997 | Fuisz et al. |
| 5,700,816 A | 12/1997 | Isakson et al. |
| 5,811,446 A | 9/1998 | Thomas |
| 5,824,658 A | 10/1998 | Falk et al. |
| 5,886,030 A | 3/1999 | Maniar |
| 5,962,012 A | 10/1999 | Lin et al. |
| 6,046,191 A | 4/2000 | Hamley et al. |
| 6,071,539 A | 6/2000 | Robinson et al. |
| 6,090,800 A | 7/2000 | Unger et al. |
| 6,106,862 A | 8/2000 | Chen et al. |
| 6,136,804 A | 10/2000 | Nichtberger |

(Continued)

FOREIGN PATENT DOCUMENTS

| | | |
|---|---|---|
| AU | 673675 B2 | 11/1996 |
| CA | 1102802 | 6/1981 |
| CA | 2164100 A1 | 1/1995 |
| CA | 2166204 A1 | 1/1995 |
| CA | 2264626 A1 | 3/1998 |
| CA | 2326517 A1 | 10/1999 |
| CA | 2404360 A1 | 9/2001 |
| CA | 2414063 A1 | 12/2001 |
| CA | 2469588 | 6/2003 |
| CA | 2503396 A1 | 5/2004 |

(Continued)

OTHER PUBLICATIONS

Saha et al., "Effect of solubilizing excipients on permeation of poorly water-soluble compounds across Caco-2 cell monolayers". European Journal of Pharmaceutics and Biopharmaceutics, vol. 50, No. 3, 2000, pp. 403-411, Abstract accessed at http://cat.inist.fr/?aModele=afficheN&cpsidt=798854, accessed on Aug. 13, 2010, 3 pages.

(Continued)

*Primary Examiner* — Mina Haghighatian
(74) *Attorney, Agent, or Firm* — Michael P. Morris; Joyce L. Morrison

(57) ABSTRACT

A plastic container containing a pharmaceutical composition comprising benzoic acid or a derivative or a pharmaceutically acceptable salt thereof and a COX-inhibitor of the oxicam-type or a pharmaceutical acceptable salt thereof, wherein the container material selected from one or more members of the group consisting of a homopolymer of polypropylene (PP), a copolymer of polypropylene (PP), a homopolymer of polyethylene terephthalate (PET) and a copolymer of polyethylene terephthalate (PET), and optionally one or more non-polymeric components.

15 Claims, 10 Drawing Sheets

(56) References Cited

U.S. PATENT DOCUMENTS

| | | | |
|---|---|---|---|
| 6,156,349 | A | 12/2000 | Steinbach et al. |
| 6,166,012 | A | 12/2000 | Muller et al. |
| 6,180,136 | B1 | 1/2001 | Larson et al. |
| 6,183,779 | B1 | 2/2001 | Ouali et al. |
| 6,184,220 | B1 | 2/2001 | Turck et al. |
| 6,187,800 | B1 | 2/2001 | Suri et al. |
| 6,221,377 | B1 | 4/2001 | Meyer |
| 6,284,269 | B1 | 9/2001 | Struengmann et al. |
| 6,319,519 | B2 | 11/2001 | Woolfe et al. |
| 6,495,603 | B1 | 12/2002 | Miyake et al. |
| 6,550,955 | B2 | 4/2003 | D'Silva |
| 6,599,529 | B1 | 7/2003 | Skinhøj et al. |
| 6,605,295 | B1 | 8/2003 | Bellmann et al. |
| 6,630,056 | B1 | 10/2003 | Thibierge et al. |
| 6,669,957 | B1 | 12/2003 | Laruelle et al. |
| 6,682,747 | B1 | 1/2004 | Turck et al. |
| 6,869,948 | B1 | 3/2005 | Bock et al. |
| 6,986,346 | B2 | 1/2006 | Hochrainer et al. |
| 7,105,512 | B2 | 9/2006 | Morizono et al. |
| 7,969,206 | B2 | 6/2011 | Ito |
| 2002/0006440 | A1 | 1/2002 | Cherukuri |
| 2002/0016342 | A1 | 2/2002 | Scolnick et al. |
| 2002/0035107 | A1 | 3/2002 | Henke et al. |
| 2002/0058908 | A1 | 5/2002 | Zierenberg et al. |
| 2002/0068088 | A1 | 6/2002 | Gruber |
| 2002/0077328 | A1 | 6/2002 | Hassan et al. |
| 2002/0099049 | A1 | 7/2002 | Burch et al. |
| 2002/0106345 | A1 | 8/2002 | Uhrich et al. |
| 2002/0187187 | A1 | 12/2002 | Ohki et al. |
| 2003/0050305 | A1 | 3/2003 | Tejada |
| 2003/0055051 | A1 | 3/2003 | Morizono et al. |
| 2003/0109701 | A1 | 6/2003 | Coppi et al. |
| 2003/0119825 | A1 | 6/2003 | Folger et al. |
| 2003/0199482 | A1 | 10/2003 | Seibert et al. |
| 2003/0220306 | A1 | 11/2003 | Simmons et al. |
| 2004/0001883 | A1 | 1/2004 | Matsui et al. |
| 2004/0015126 | A1 | 1/2004 | Zierenberg et al. |
| 2004/0024041 | A1 | 2/2004 | Selzer |
| 2004/0024042 | A1 | 2/2004 | Breyer |
| 2004/0037869 | A1 | 2/2004 | Cleverly et al. |
| 2004/0043992 | A1 | 3/2004 | Tolba et al. |
| 2004/0110747 | A1 | 6/2004 | Altman |
| 2004/0171611 | A1 | 9/2004 | Trummlitz et al. |
| 2004/0180092 | A1 | 9/2004 | Henke et al. |
| 2004/0198826 | A1 | 10/2004 | Baiker et al. |
| 2004/0204413 | A1 | 10/2004 | Faour et al. |
| 2004/0204472 | A1 | 10/2004 | Briggs et al. |
| 2004/0214753 | A1 | 10/2004 | Britten et al. |
| 2004/0229038 | A1 | 11/2004 | Cooper et al. |
| 2004/0234596 | A1 | 11/2004 | Ohki et al. |
| 2004/0253312 | A1 | 12/2004 | Sowden et al. |
| 2005/0038018 | A1 | 2/2005 | Kanbe et al. |
| 2005/0147664 | A1 | 7/2005 | Liversidge et al. |
| 2005/0187212 | A1 | 8/2005 | Ohki et al. |
| 2005/0187213 | A1 | 8/2005 | Lang et al. |
| 2005/0197332 | A1 | 9/2005 | Altman |
| 2005/0244491 | A1 | 11/2005 | Ohki et al. |
| 2005/0245510 | A1 | 11/2005 | Friton et al. |
| 2005/0277634 | A1 | 12/2005 | Janott et al. |
| 2005/0288280 | A1 | 12/2005 | Friton et al. |
| 2006/0079516 | A1 | 4/2006 | Henke et al. |
| 2006/0160793 | A1 | 7/2006 | Altman |
| 2006/0217431 | A1 | 9/2006 | Daemmgen et al. |
| 2007/0074296 | A1 | 4/2007 | Folger et al. |
| 2007/0099907 | A1 | 5/2007 | Altman |
| 2007/0193894 | A1 | 8/2007 | Macken et al. |
| 2007/0249727 | A1 | 10/2007 | Martin et al. |
| 2008/0132493 | A1 | 6/2008 | Folger et al. |
| 2008/0234380 | A1 | 9/2008 | Shapiro |
| 2008/0280840 | A1 | 11/2008 | Lang et al. |
| 2011/0083985 | A1 | 4/2011 | Folger et al. |
| 2011/0275618 | A1 | 11/2011 | Folger et al. |
| 2012/0077764 | A1 | 3/2012 | Freehauf et al. |
| 2013/0178467 | A1 | 7/2013 | Henke et al. |
| 2014/0066440 | A1 | 3/2014 | Folger et al. |
| 2014/0113893 | A1 | 4/2014 | Folger et al. |

FOREIGN PATENT DOCUMENTS

| | | |
|---|---|---|
| DE | 3434707 A1 | 4/1985 |
| DE | 3700172 A1 | 7/1987 |
| DE | 4217971 C1 | 10/1993 |
| DE | 19729879 A1 | 1/1999 |
| DE | 10010123 A1 | 9/2001 |
| DE | 10024752 A1 | 11/2001 |
| DE | 10032132 A1 | 1/2002 |
| DE | 10300323 A1 | 10/2004 |
| EP | 0002482 B2 | 6/1979 |
| EP | 0034432 A2 | 8/1981 |
| EP | 0093999 A2 | 11/1983 |
| EP | 0177870 A2 | 4/1986 |
| EP | 0179430 A2 | 4/1986 |
| EP | 0306984 A1 | 3/1989 |
| EP | 0360246 A1 | 3/1990 |
| EP | 0390071 A1 | 10/1990 |
| EP | 0422681 A1 | 4/1991 |
| EP | 0465235 A1 | 1/1992 |
| EP | 0560329 A1 | 9/1993 |
| EP | 0629392 A1 | 12/1994 |
| EP | 0945134 A1 | 9/1999 |
| EP | 1082966 A1 | 3/2001 |
| EP | 1190714 A2 | 3/2002 |
| EP | 1568369 A1 | 8/2005 |
| ES | 2065846 A1 | 2/1995 |
| ES | 2159564 T3 | 10/2001 |
| FR | 2437838 A1 | 4/1980 |
| GB | 2455875 A | 6/2009 |
| IT | 1251650 B | 5/1995 |
| JP | 47007352 Y1 | 3/1972 |
| JP | 1299230 A | 12/1989 |
| JP | 2001170083 A | 6/2001 |
| JP | 2003535902 A | 12/2003 |
| JP | 3550782 B2 | 8/2004 |
| JP | 4018022 B2 | 12/2007 |
| JP | 04321624 B2 | 8/2009 |
| WO | 9301814 A1 | 2/1993 |
| WO | 9400420 A1 | 1/1994 |
| WO | 9509639 A1 | 4/1995 |
| WO | 9517178 A1 | 6/1995 |
| WO | 9518604 A1 | 7/1995 |
| WO | 9603387 A1 | 2/1996 |
| WO | 9603388 A1 | 2/1996 |
| WO | 9610999 A2 | 4/1996 |
| WO | 9611192 A1 | 4/1996 |
| WO | 9641625 A1 | 12/1996 |
| WO | 9703655 A1 | 2/1997 |
| WO | 9703667 A1 | 2/1997 |
| WO | 9717978 A1 | 5/1997 |
| WO | 9717989 A1 | 5/1997 |
| WO | 9729776 A1 | 8/1997 |
| WO | 9731631 A1 | 9/1997 |
| WO | 9817250 A1 | 4/1998 |
| WO | 9909988 A1 | 3/1999 |
| WO | 9912524 A1 | 3/1999 |
| WO | 9927906 A1 | 6/1999 |
| WO | 9949845 A1 | 10/1999 |
| WO | 9949867 A1 | 10/1999 |
| WO | 9959634 A1 | 11/1999 |
| WO | 0015195 A1 | 3/2000 |
| WO | 0108689 A1 | 2/2001 |
| WO | 0137838 A1 | 5/2001 |
| WO | 0152897 A2 | 7/2001 |
| WO | 0164268 A1 | 9/2001 |
| WO | 0187343 A2 | 11/2001 |
| WO | 0197813 A2 | 12/2001 |
| WO | 02085331 A1 | 10/2002 |
| WO | 03049733 A1 | 6/2003 |
| WO | 03082297 A1 | 10/2003 |
| WO | 03097066 A1 | 11/2003 |
| WO | 2004004776 A1 | 1/2004 |
| WO | 2004026116 A2 | 4/2004 |
| WO | 2004026313 A1 | 4/2004 |
| WO | 2004037264 A1 | 5/2004 |
| WO | 2004089379 A2 | 10/2004 |

(56) References Cited

FOREIGN PATENT DOCUMENTS

| WO | 2004103283 | A2 | 12/2004 |
|---|---|---|---|
| WO | 2005002542 | A2 | 1/2005 |
| WO | 2005004915 | A2 | 1/2005 |
| WO | 2005079806 | A1 | 9/2005 |
| WO | 2005097040 | A1 | 10/2005 |
| WO | 2005105101 | | 11/2005 |
| WO | 2005115386 | A1 | 12/2005 |
| WO | 2006000306 | A1 | 1/2006 |
| WO | 2006100213 | A1 | 9/2006 |
| WO | 2007039417 | A1 | 4/2007 |
| WO | 2007087214 | A1 | 8/2007 |
| WO | 2008152122 | A2 | 12/2008 |
| WO | 2009049304 | A1 | 4/2009 |
| WO | 2011046853 | A1 | 4/2011 |
| WO | 2011107498 | A1 | 9/2011 |
| WO | 2011138197 | A2 | 11/2011 |

OTHER PUBLICATIONS

Schneeweis et al., "In Vivo and In Vitro Diclofenac Sodium Evaluation After Rectal Application of Soft Gelatine Capsules Enabling Application Induced Transformation (AIT) into a Seminsolid System of Liquid Crystals (SSLC) for Controlled Release". Pharmaceutical Research, vol. 14, No. 12, Dec. 1997, pp. 1726-1729.
Sciencelab.com, "Lactose, Monohydrate, Spray-Dried Powder, NF". Accessed at http://www.epoxy-paint.net/page/.S/PVAR/10419/SLL1453, Feb. 29, 2008, 2 pages.
Sorbera et al., "Lumiracoxib Antiarthritic, COX-2 Inhibitor". Drugs of the Future, vol. 27, No. 8, Aug. 2002, pp. 740-747.
Stei et al., "Local Tissue Tolerability of Meloxicam, a New NSAID: Indications for Parental, Dermal and Mucosal Administration". British Journal of Rheumatology, vol. 35, Supp. 1, 1996, pp. 44-50.
Straus et al., "New Evidence for Stroke Prevention: Clinical Applications". The Journal of the American Medical Association, vol. 288, No. 11, Sep. 2002, pp. 1396-1398.
Straus et al., "New Evidence for Stroke Prevention: Scientific Review". The Journal of the American Medical Association, vol. 288, No. 11, Sep. 2002, pp. 1388-1395.
Sunose et al., "The Effect of Cyclooxygenase 2 Inhibitor, FK3311, on Ischemia-Reperfusion Injury in Canine Lung Transplantation". Journal of Heart and Lung Transplantation, vol. 19, No. 1, Jan. 2000, p. 40.
Tuerck et al., "Clinical Pharmacokinetics of Meloxicam". Arzneimittel-Forschung, vol. 47, No. 3, 1997, pp. 253-258.
Tunuguntla et al., "Management of Prostatitis". Prostate Cancer and Prostatic Diseases, vol. 5, No. 3, 2002, pp. 172-179.
Vippagunta et al., "Crystalline solids". Advanced Drug Delivery Reviews, vol. 48, 2001, pp. 3-26.
Wagenlehner et al., "Therapy of Prostatitis Syndrome". Der Urologe [A], vol. 40, No. 1, 2001, pp. 24-28. [English Abstract at p. 25].
Abstract in English of JP2001170083, 2001.
Abstract in English of JP4018022, 2007.
Abstract in English of JP3550782, 2004.
Abstract in English of WO199301814, 1993.
Chemical Abstracts, vol. 118, No. 18, Abstract No. 175803, XP002087682, 1993, 1 page.
Abstract in English of ES2065846, 1995.
Gerritsen et al., "Prostaglandin Synthesis and Release from Cultured Human Trabecular-meshwork Cells and Scleral Fibroblasts". Experimental Eye Research, vol. 43, No. 6, 1986, pp. 1089-1102.
Herbort et al., "Anti-inflammatory Effect of Topical Diclofenac After Argon Laser Trabeculoplasty: Preliminary Results of a Placebo Controlled Study". Klin. Monatsbl. Augenheik, vol. 200, No. 5, May 1992, pp. 358-361.
Pharma Projects, Dialog File 928, Accession Nr. 0021312, Diclofenac, InSite Vision, 1996, 5 pages.
Snyder et al., "Corticosteroid Treatment and Trabecular Meshwork Proteases in Cell and Organ Culture Supernatants". Experimental Eye Research, vol. 57, No. 4, 1993, pp. 461-468.
Masferrer et al., "Cyclooxygenase-2 Inhibitors: A New Approach to the Therapy of Ocular Inflammation". Survey of Ophthalmology, vol. 41, Supp. 2, Feb. 1997, pp. S35-S40.
Abstract in English for IT1251650, 1995.
Li et al., "Degradation mechanism and kinetic studies of a novel anticancer agent, AG2034". International Journal of Pharmaceutics, vol. 167, 1998, pp. 49-56.
Bunji, Kouho, "Tissue Damage Due to Infections". Drug Injection Handbook, Fundamentals of Blending Variation for Injection Drugs, Nanzando Co. Ltd., Tokyo, 1976, p. 5.
Pharmaceutical Excipent Encyclopedia, Yakuji Nippo Ltd., Tokyo, 1994, pp. 2-5.
Nell et al., "Comparison of vedaprofen and meloxicam in dogs with muskuloskeletal pain and inflammation". Journal of Small Animal Practice, vol. 43, No. 5, May 2002, pp. 208-212 [Accessed at http://www.ncbi.nlm.nih.gov/pubmed/12038853 on Sep. 27, 2013]. Abstract Only, 1 page.
"Committee for Veterinary Medicinal Products—Meloxicam (Extension to PIGS)—Summary Report (5)". The European Agency for the Evaluation of Medicinal Products, Veterinary Medicines and Information Technology, Dec. 2000, pp. 1-3.
"Metacam (R) 0.5 mg/ml oral suspension for cats." Boehringer Ingelheim Datasheet, Web site: http://www.vetgb.com/yetgb_pdfs/metacamc_7a5c_vetgb.pdf> Accessed on Jun. 8, 2010.
"Metacam Professional Insert: Metacam® (meloxicam) 1.5 mg/mL Oral Suspension (equivalent to 0.05 mg per drop) Non-Steroidal anti-inflammatory drug for oral use in dogs only". Boehringer Ingelheim, Jan. 2005, 2 pages.
"Metacam(R)" FDA Animal & Veterinary Drug Labels, Web site: http://www.fda.gov/downloads/AnimalVeterinary/Products/ApprovedAnimalDrugProducts/DrugLabels/UCM050397.pdf> Accessed Jun. 8, 2010.
"Types of Solutions". University of Wisconsin, Stevens Point, Feb. 1, 2001, accessed at http://www.uwsp.edu/chemistry/tzamis/chem106pdfs/solutionexamples.pdf, Google date sheet included, 2 pages.
Abstract in English of DE10024752, 2001.
Abstract in English of DE3434707, 1985.
Abstract in English of FR2437838, 1980.
Abstract in English of JP02906528, 1999.
Abstract in English of JP11139971, 1999.
Abstract in English of JP47007352, 1972.
Altman et al., "Efficacy Assessment of Meloxicam, a Preferential Cyclooxygenase-2 Inhibitor, in Acute Coronary Syndromes Without ST-Segment Elevation: The Nonsteroidal Anti-Inflammatory Drugs in Unstable Angina Treatment-2 (NUT-2) Pilot Study". Circulation, vol. 106, 2002, pp. 191-195.
Ansel et al., "Pharmaceutical Dosage Forms and Drug Delivery Systems". Seventh Edition, Lippincott Williams & Wilkins, Philadelphia, PA, 1999, pp. 77-87.
Bednarek et al., "Effect of steroidal and non-steroidal anti-imflammatory drugs in combination with long-acting oxytetracycline on non-specific immunity of calves suffering from enzootic bronchopneumonia". Veterinary Microbiology, vol. 96, 2003, pp. 53-67.
Bednarek et al., "The effect of steroidal and non-steroidal anti-inflammatory drugs on the cellular immunity of calves with experimentally-induced local lung inflammation". Veterinary Immunology and Immunopathology, vol. 71, 1999, pp. 1-15.
Boehringer Ingelheim; Metacam (Meloxicam) Now Approved for Pigs and Mastitis in Dairy Cows; May 2003 Press Release; pp. 1-2.
Cho et al., "In vitro effects of *Actinobacillus pleuropneumoniae* on inducible nitric oxide synthase and cyclooxygenase-2 in porcine alveolar macrophages". American Journal of Veterinary Research, vol. 64, No. 12, Dec. 2003, pp. 1514-1518.
Clarke et al., "Feline osteoarthritis: a prospective study of 28 cases". Journal of Small Animal Practice, vol. 47, 2006, pp. 439-445.
D'Yakov et al., "Long term use of Tamsulosin (omnic®) in Patients with Chronic Prostatitis". Urologiia, vol. 5, 2002, pp. 10-12.
Del Tacca et al., "Efficacy and Tolerability of Meloxicam, a COX-2 Preferential Nonsteroidal Anti-Inflammatory Drug". Clinical Drug Investigation, vol. 22, No. 12, 2002, pp. 799-818.

(56) References Cited

OTHER PUBLICATIONS

Dellabella et al., "Conservative Managment of Juxtavesical Calculi with Tamsulosin". European Urology Supplements, vol. 2, No. 1, 2003, p. 81.
DOW Chemicals Brochure, entitled "Using METHOCEL cellulose ethers for controlled release of drugs in hyrophilic matrix systems." Publication Jul. 2000, Form No. 198-02075-700 AMS, pp. 1-36.
Dunn et al., "Tamsulosin: A Review of its Pharmacology and Therapeutic Efficacy in the Management of Lower Urinary Tract Symptoms". Drugs & Aging, vol. 19, No. 2, 2002, pp. 132-161.
Engelhardt et al., "Meloxicam: Influence on Arachidonic Acid Metabolism". Biochemical Pharmacology, vol. 51, 1996, pp. 21-28.
Ettmayer et al., "Lessons Learned from Marketed and Investigational Prodrugs". Journal of Medicinal Chemistry, vol. 47, No. 10, May 2004, pp. 2393-2404.
Farkouh et al., "Comparison of lumiracoxib with naproxen and ibuprofen in the Therapeutic Arthritis Research and Gastrointestinal Event Trial (TARGET), cardiovascular outcomes: randomised controlled trial". Lancet, vol. 364, Aug. 2004, pp. 675-684.
Fitzgerald et al., "COX-2 inhibitors and the cardiovascular system". Clinical and Experimental Rheumatology, vol. 19, No. 6, Supp. 25, Nov. 2001, pp. S31-S36.
Fitzpatrick et al., "Recognising and Controlling Pain and Inflammation in Mastitis". Proceedings of the British Mastitis Conference, Axient/Institute for Animal Health, Milk Development Council/Novartis Animal Health, 1998, pp. 36-44.
Giuliani et al., "Role of Antithrombotic Therapy in Cardiac Disease". Mayo Clinic Practice of Cardiology, Third Edition, Mosby, St. Louis, MO, 1996, pp. 1116-1121.
Gollackner et al., "Increased apoptosis of hepatocyctes in vascular occulusion after orthotopic liver transplantation". Transplant International, vol. 13, No. 1, 2000, pp. 49-53.
Gruet et al., "Bovine mastitis and intramammary drug delivery: review and perspectives". Advanced Drug Delivery Reviews, vol. 50, 2001, pp. 245-259.
Guth et al., "Pharmacokinetics and pharmacodynamics of terbogrel, a combined thromboxane A2 receptor and synthase inhibitor, in healthy subjects". British Journal of Clinical Pharmacology, vol. 58, No. 1, Jul. 2004, pp. 40-51.
Hawkey et al., "Gastrointestinal Tolerability of Meloxicam Compared to Diclofenac in Osteoarthritis Patients". British Journal of Rheumatology, vol. 37, No. 9, 1998, pp. 937-945.
Hirsch et al, "Investigation on the efficacy of meloxicam in sows with mastitis-metritis-agalactia syndrome". Journal of Veterinary Pharmacology and Therapeutics, vol. 26, 2003, pp. 355-360.
Hydrated Silica Webpage; http://science.kosmix.com/topic/hydrated_silica; Kosmix Corporation, Apr. 21, 2011, pp. 1-14.
International Search Report and Written Opinion for PCT/US2010/052128 mailed on Jan. 27, 2011.
Jain et al., "Antiplatelet therapy in acute coronary syndromes without persistent ST-segment elevation". Cardiovascular Drugs and Therapy, vol. 15, No. 5, Sep. 2001, pp. 423-436. [Abstract Only].
Kimura et al., "Effect of cilostazol on platelet agrregation and experimental thrombosis". Arzneimittel-Forschung, vol. 35, No. 7A, 1985, pp. 1144-1149. [Abstract Only].
Kumar et al., "Comparative Studies on Effect of Some Hydrophilic Polymers on the Dissolution Rate of a Poorly Water Soluble Drug, Meloxicam". Indian Drugs, vol. 39, No. 6, Apr. 2002, pp. 323-329.
Lieberman et al., "Tablet Formulation and Design" in Pharmaceutical Dosage Forms: Tablets, vol. 1, Second Edition, Marcel Dekker, Inc., New York, New York, 1989, pp. 105-108.
Luger et al., "Structure and physicochemical properties of meloxicam, a new NSAID". European Journal of Pharmaceutical Sciences, vol. 5, 1996, pp. 175-187.
Macdonald Campus of McGill University, "Mastitis in Dairy Cows", published online, Jul. 2003, pp. 1-12.
Mcdonald et al., "Calpain inhibitor I reduces the activation of nuclear factor-KappaB and Organ Injury/Dysfunction in Hemorrhagic Shock". The FASEB Journal, vol. 15, Jan. 2001, pp. 171-186.
Noble et al., "Meloxicam". Drugs, vol. 51, No. 3, Mar. 1996, pp. 424-430.
Parikh et al., Binders and Solvents, Chapter 4, Handbook of Pharmaceutical Granulation Technology, First Edition, Marcel Dekker,1997, pp. 59-67.
Physicians' Desk Reference, 55th Edition, Medical Economics Company, Inc., 2001, pp. 981-984 and pp. 1404-1406.
Rantanen et al., "Process Analysis of Fluidized Bed Granulation". AAPS PharmsciTech, vol. 2, No. 4, Article 21, 2001, 8 pages.
Remington: The Science and Practice of Pharmacy, 19th Edition, vol. II, Mack Publishing Company, Easton, Pennsylvania, 1995, p. 1646.
Robson et al., "Intrinsic acute renal failure (ARE) associated with non-steroidal anti-inflammatory drug (NSAId) use in juvenile cats undergoing routine desexing—16 cases 1998-2005". May 2006, Journal of Veterinary Internal Medicine, vol. 20, No. 3, Abst. 109, p. 740.
Rudnic et al., "Oral Solid Dosage Forms"., Gennaro, Editior, Remington's Pharmaceutical Sciences, 18th Edition, Mack Publishing Company, Easton, PA, 1990, pp. 1633-1645 and pp. 1654-1655.

CONTAINERS FOR COMPOSITIONS COMPRISING MELOXICAM

CROSS REFERENCE TO RELATED APPLICATIONS

This application claims priority to U.S. Nonprovisional application Ser. No. 12/901,649, filed 11 Oct. 2010 and entitled "Containers for Compositions Comprising Meloxicam," which claims priority to provisional application No. 61/250,709, filed 12 Oct. 2009 and entitled "Containers for Compositions Containing Meloxicam." The disclosure of each of these applications is incorporated herein by reference in its entirety.

TECHNICAL FIELD

This invention relates to containers for storage, dispensing and preservation of compositions containing meloxicam.

BACKGROUND OF THE INVENTION

Some pharmaceutical compositions as for example injectable compositions require to be sterilised prior to administration. These pharmaceutical compositions have to be manufactured and stored under sterile conditions. A multi-layered plastic polymeric container for the storage of a chemical composition that may or may not be sterilised is disclosed in WO2008/152122. The herein disclosed bottles have a volume of 50 ml to 500 ml. A plastic container made of polyethylene naphthylate with a closure device for storing and preserving a composition of sodium benzoate and cefdinir is disclosed in WO2007/087214.

It is crucial that the material of the container is pharmaceutically acceptable meaing that it should not interfere with the pharmaceutical composition or alter the quality of the compositions. The reverse must also be valid, that the pharmaceutical compositions should not interfere or alter the nature and/or composition of the container. Any alterations that may occur can result in the migration of chemicals from and to the container material and/or the pharmaceutical composition. Any chemicals from the container material that may mix with the solution will be impurities within the solution that may affect the solution by degrading the composition or may not be tolerated in any other way. Degradation may also occur over time under the action of oxygen, light and/or temperature. If the container and/or solution has been sterilised by for example irradiation, then this may also result in degradation of any of the material. The chemical properties of the pharmaceutical composition, such as the stability of the active ingredient may alter over time because of any interactions and thus reduce the lifetime of the formulation. Another interaction that has to be avoided is adsorption of any of the components, especially sodium benzoate, within the solution to the material of the bottle.

The pharmaceutical composition comprising meloxicam is a very frequently used drug for veterinary medicine for the treatment of for example pain, post-operative pain, inflammation, fever, diarrhoea, lameness, problems with the locomotor apparatus, respiratory complaints, osteoarthritis. It is available not only in different formulations but also in dosage forms which are optimised for the use of a pharmaceutical composition for several animal species.

Oral suspensions of meloxicam with a concentration of 1.5 mg/ml are established for the treatment of dogs for more than 10 years. This formulation is revealed in the patent application WO99/49845.

In addition it was found that the drug is suitable for the treatment of cats as well. The palatability of the formulation in both dogs and cats is exceptional, thus ensuring an excellent compliance of drug treatment. For cats an oral suspension with 0.5 mg/ml of meloxicam has been developed, which allows accurate dosing according to the body weight of the animal.

Oral suspension of 0.5 mg/ml meloxicam for chronic treatment has been approved. This suspension is available in 25 ml high-density polyethylene (HDPE) bottles filled with 15 ml of the suspension. For both the 1.5 mg/ml and the 0.5 mg/ml suspension a decrease of the sodium benzoate content over time can be observed. It could be proven that this loss of the preservative is explained not by chemical degradation, but by adsorption of sodium benzoate to the bottle wall. Sodium benzoate is used as the preservative and is the only substance of the solution, which can be active as a preservative and because of its adsorption it needed to be assessed whether the formulation is still adequately preserved over the shelf-life of the product. It could be demonstrated that at a sodium benzoate content of 70% of the label claim of 0.15 mg/ml the formulation is still fulfilling all requirements of the European Pharmacopoeia for preservative efficacy. This approach of increasing the preservative in order to prolong the potential shelf-life of the formulation is undesirable as it cannot be completely excluded that preservatives may cause irritation or allergic reactions. It would be an unnecessary amount of preservatives that would be given to the animals.

For the acute treatment in cats a smaller bottle is required which contains enough of the pharmaceutical solution for the treatment of up to five (5) days. A container with approximately three (3) ml of an oral suspension comprising 0.5 mg/ml meloxicam would fulfil these requirements. In addition such a composition would allow the treatment of several other species like small dogs (with a body weight of 0.5 kg up to 5 kg), rabbits and guinea pigs. Thus the problem underlying the present invention was to provide a plastic container containing a pharmaceutical composition comprising benzoic acid or a derivative thereof or a pharmaceutical acceptable salt thereof and a COX-inhibitor of the oxicam-type or a pharmaceutical acceptable salt thereof avoiding a significant loss of benzoic acid or a derivative thereof during storage. Furthermore, the problem underlying the present invention was to provide a plastic container containing a pharmaceutical composition comprising sodium benzoate and meloxicam avoiding a significant loss of sodium benzoate during storage.

SUMMARY OF THE INVENTION

The present invention relates to a plastic container containing a pharmaceutical composition comprising benzoic acid or a derivative thereof or a pharmaceutical acceptable salt thereof and a COX-inhibitor of the oxicam-type or a pharmaceutical acceptable salt thereof, wherein the container material is selected from one or more members of the group consisting of a homopolymer of polypropylene (PP), a copolymer of polypropylene (PP), a homopolymer of polyethylene terephthalate (PET) and a copolymer of polyethylene terephthalate (PET), and optionally non-polymeric components. This container stores and/or preserves a pharmaceutical composition comprising sodium benzoate and meloxicam or a pharmaceutical acceptable salt thereof, wherein the container material is constituted of polypropylene (PP) or polyethylene terephthalate (PET), i.e. the container material is selected from the group consisting of homopolymer of polypropylene (PP), copolymer of polypropylene (PP), homopolymer of polyethylene terephthalate (PET) and copolymer of polyethylene terephthalate (PET), and optionally non-polymeric components. The container also includes a closure device for storing and preserving a pharmaceutical composition, which can also be connected to a dispensing device.

The plastic container for storing, preserving and/or dispensing a pharmaceutical composition comprising sodium benzoate and meloxicam or a pharmaceutical acceptable salt thereof has a volume of 3 to 11 ml with a total volume of the liquid composition of 2 ml to 10 ml.

The pharmaceutical composition that is stored and preserved within the bottle is a meloxicam-containing composition with meloxicam in a concentration of 0.2 mg/ml to 20 mg/ml. The pharmaceutical composition also comprises sodium benzoate in the concentration range of 0.8 mg/ml to 2.0 mg/ml.

Surprisingly the combination of the container according to the current invention and the pharmaceutical composition comprising meloxicam and sodium benzoate enables the composition to remain substantially stable over 18 months or at least 18 months.

DETAILED DESCRIPTION OF THE INVENTION

Figure 1:
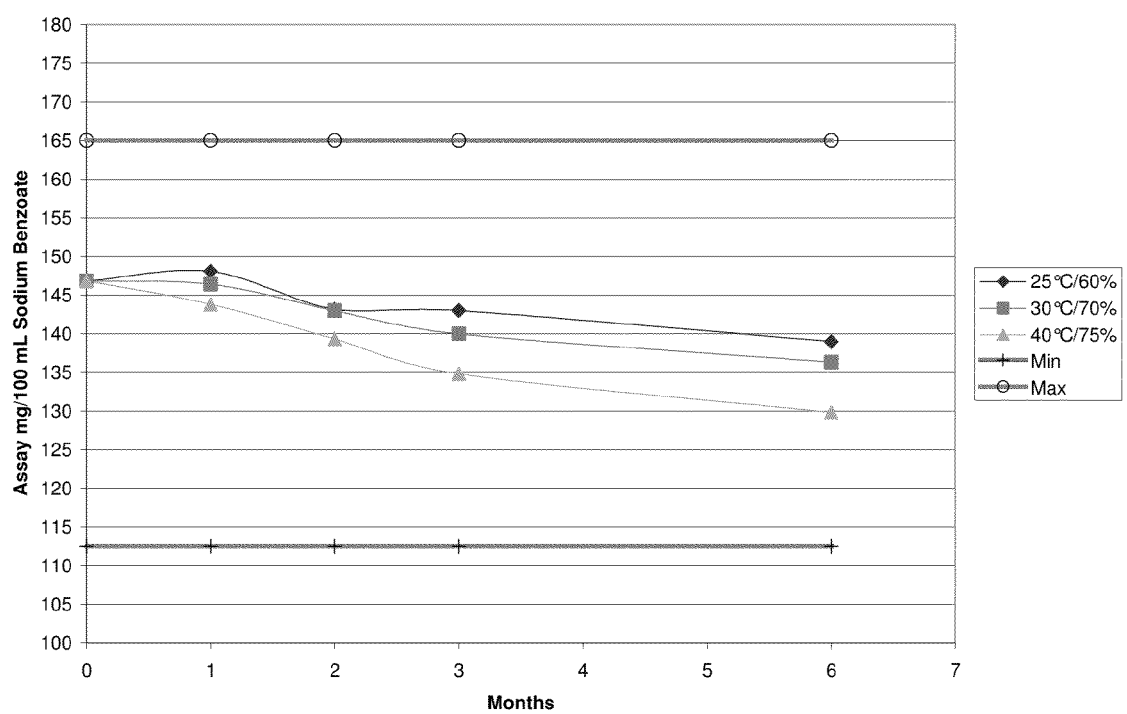
FIG. 1: PET Bottles—Sodium Benzoate Content over Storage Time

The present invention relates to a plastic container containing a pharmaceutical composition comprising benzoic acid, a derivative or pharmaceutically acceptable salt thereof and an oxicam or a pharmaceutical acceptable salt thereof, characterised in that the container material is polypropylene (PP) or polyethylene terephthalate (PET). The plastic container is made of container material containing plastic/polymers such as PP or PET and optionally one or more, preferably one or two, most preferably one, non-polymeric components. Furthermore, the present invention relates to a plastic container containing a pharmaceutical composition comprising benzoic acid, a derivative or pharmaceutically acceptable salt thereof and a COX-inhibitor of the oxicam-type or a pharmaceutical acceptable salt thereof, wherein the container material is selected from one or more members, preferably one member, of the group consisting of a homopolymer of polypropylene (PP), a copolymer of polypropylene (PP), a homopolymer of polyethylene terephthalate (PET) and a copolymer of polyethylene terephthalate (PET), and optionally one or more non-polymeric components. The present invention also relates to a plastic container containing a pharmaceutical composition comprising sodium benzoate and meloxicam or a pharmaceutical acceptable salt thereof, wherein the container material is selected from one or more members, preferably one member, of the group consisting of a homopolymer of polypropylene (PP), a copolymer of polypropylene (PP), a homopolymer of polyethylene terephthalate (PET) and a copolymer of polyethylene terephthalate (PET), and optionally one or more non-polymeric components. The container is equipped with a closure device for storage and preservation of a pharmaceutical composition. The container allows a stable preservation of said composition for 18 months or at least 18 months. Throughout the whole specification, by the terms polypropylene (PP) is meant a homopolymer, one or more copolymers or a combination thereof, especially random copolymers. Throughout the whole specification, by the terms polyethylene terephthalate (PET) is meant a homopolymer, one or more copolymers or a combination thereof, especially random copolymers.

A vast variety of polymeric materials are commonly used for containers or packaging, which contain pharmaceutical compositions such as for example polyvinyl chloride (PVC), poly(ethylene-vinyl acetate) or any other polyolefin. Different types of containers made from different polymers are not suitable for the use in the current invention such as high-density polyethylene (HDPE), low-density polyethylene (LDPE), polycarbonate (PC) or glass. Only the material according to the current invention, polypropylene (PP) and polyethylene terephthalate (PET), is usable and fulfils for purpose of the invention. Different types of PP are suitable for the intended purpose such as but not limited to Purell RP270G white (Basell), RB845MO (Borealis), PPM R021 (Total Atofina). It has been surprisingly found that polypropylene and polyethylene terephthalate but particularly polypropylene does not result in any adsorption of the preservative from the solution onto the wall of the bottle and thus leads to an increased stability of the solution. Thus the invention relates to a plastic container containing a pharmaceutical composition comprising sodium benzoate and meloxicam or a pharmaceutical acceptable salt thereof, wherein the container material is polypropylene (PP) or polyethylene terephthalate (PET) with the purpose of storing and/or preserving a pharmaceutical composition. The container further comprises a closure device for storing and preserving a pharmaceutical composition. A suitable closure is e.g. a two-piece tamper-proof and child-resistant closure. A suitable type is e.g. a cap type LT.9171 supplied by Gerresheimer Boleslawiec S.A., Boleslawiec, Poland.

The inventions also relates to an oral dispenser of the pharmaceutical composition that can be connected to the container, which allows a precise administration of the pharmaceutical composition. Thus the bottle according to the invention is suitable for connecting a dispenser to the bottle opening. Due to the necessity of accurate but flexible dosing according to the body weight of the animal to be treated, oral dispensers are the first choice for administration of a specific volume of the formulation from the bottle. For this purpose plastic materials are more suitable due to the fact that the containers are slightly collapsible so that the pressure differences by pulling of a certain volume of liquid from the bottle can be neglected. The material of this dispensing equipment may comprise for example either polyethylene (PE), low-density polyethylene (LDPE) or high-density polyethylene (HDPE). The dispenser can be connected for administration of the pharmaceutical composition and disconnected after usage. Thus the plastic container can be connected to a dispensing device.

Figure 8:
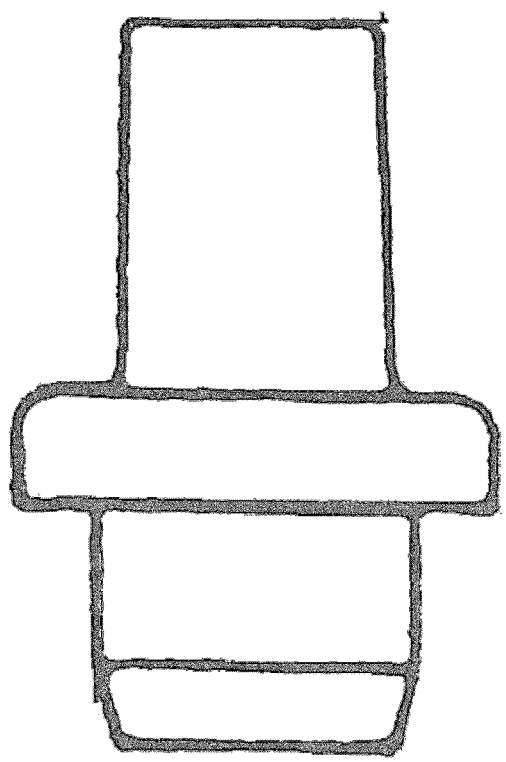
FIG. 8: Dropper provided an integrated adaptor

The dosing system as described above consists of a plastic adapter and a dosing syringe. The plastic adapter is pressed into the bottle with the bottom part. The adapter has a cylindrical and slightly conical shape. An example is given in FIG. 8. The adapter may also have a dropper function which is obtained by either a plate with a bore on the inside of the plastic part or a funnel-shaped design with a bore at the bottom of the funnel towards the bottle. When the bottle with the adapter with a dropper function is held in a horizontal to vertical position the suspension inside the bottle will flow towards the bore due to gravity and a drop will be formed and fall off. In other cases and if not required due to the dosing scheme the dropper can be designed without a bore thus allowing constant flow of liquid through the cylindrical adapter. Suitable materials for such kind of dropper adapters or tips are e.g. LDPE. Suitable adapters are commercially available as supplied by e.g. Gerresheimer.

Figure 9:
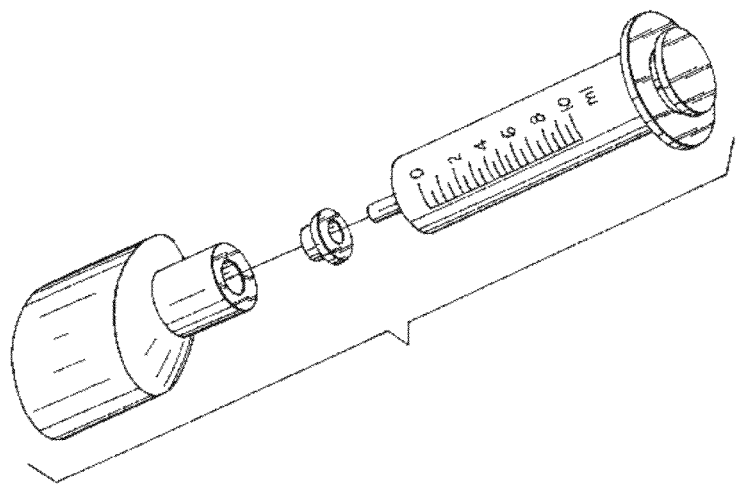
FIG. 9: Bottle-Plug-in device—Oral/Dosing Syringe
Figure 10:
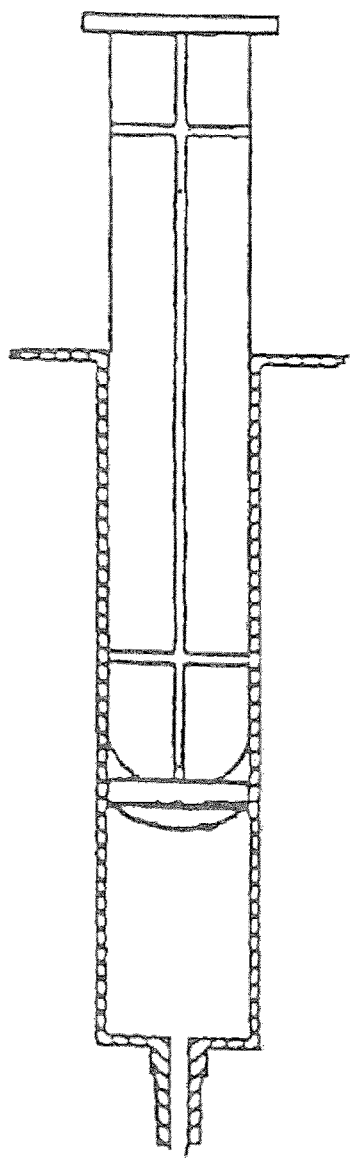
FIG. 10: Oral/Dosing syringe

In case no dropper function is required, a plug-in device can be used instead. An example is given in FIG. 9. A plug-in device is a plastic piece which is also pressed into the bottle by its bottom part. The upside is flat and has a bore in its center into which the tip of a dosing syringe fits so that a tight connection is obtained allowing to turn the bottle with the syringe docked into the plug-in upside down and pull the suspension to the required mark of the imprint of the dosing syringe. Such plug-ins may consist of e.g. LDPE. A suitable supplier can be Hubert De Backer, Sint-Niklaas, Belgium. An example of a suitable dosing syringe is given in FIG. 10. A suitable supplier can be Baxa or Hubert De Backer.

A plastic container for storing, preserving and/or dispensing a pharmaceutical composition comprising sodium benzoate and meloxicam or a pharmaceutical acceptable salt thereof wherein the liquid composition has a volume of 2 ml to 10 ml, 2.5 ml to 8 ml, 2.5 ml to 5 ml, preferably 3.5 ml to 4.5 ml, even more preferred 3 ml to 4.5 ml.

A plastic container for storing, preserving and/or dispensing a pharmaceutical composition, wherein said container has a volume of 3 ml to 11 ml, 3 ml to 10 ml, 3 ml to 8 ml, 3 ml to 5 ml, preferably 3.5 to 4.5, even more preferred containing a volume of 3 ml to 4 ml.

The container can for example have a volume of 8 ml and can contain a volume of liquid of 5 ml but is actually filled with a liquid volume of 3.5 to 4 ml in order to secure a dispensing volume of 3 ml.

A dispensing volume may be the volume that has to be guaranteed for availability and thus dosing.

Containers of the present invention may contain a solution or suspension comprising meloxicam and sodium benzoate. The preferred concentration of meloxicam in the pharmaceutical composition is 0.2 mg/ml to 20 mg/ml, preferably 0.5 mg/ml to 15 mg/ml, more preferably 0.5 mg/ml, 1.5 mg/ml or 15.0 mg/ml. The preferred concentration of sodium benzoate in the pharmaceutical composition is 0.8 mg/ml to 2.0 mg/ml, preferably 1.5 mg/ml.

The active ingredient can be any nonsteroidal anti-inflammatory drug, which is a cyclooxygenase (COX) inhibitor of the oxicam-type such as meloxicam, piroxicam, lornoxicam, tenoxicam, droxicam, isoxicam, preferably meloxicam.

The formulation used according to the invention may contain the oxicam compound as a base or a pharmaceutically acceptable salt thereof. Preferably the salt of meloxicam is selected from the group consisting of meglumine, sodium, potassium or ammonium salt, most preferably the meloxicam meglumine salt.

Other ingredients of the solution or suspension comprise commonly known agents for suspensions or solutions such as suspending agents, preservatives, flavouring agents, ph adjusters and solvents such as for example water that are used for said formulations. Specific examples for a typical suspension are displayed in table 1.

Suspending agents used may be for example organic hydrocolloid forming agents such as cellulose ether and/or silicon dioxide, preferably hydroxyethyl cellulose, hydroxypropyl cellulose, hydroxypropylmethyl cellulose and/or silicon dioxide or colloidal anhydrous silica, preferably colloidal anhydrous silica and/or hydroxyethyl cellulose.

Preservatives used may be for example benzoic acid or any derivatives or salts thereof, preferably sodium benzoate.

Flavouring agents used may be for example sugar alcohols such as glycerol, sorbitol, mannitol, xylitol or artificial sweeteners such as saccharin or any of its salt, cyclamate, aspartame, sucralose, taumatin, or any of their salts, acesulfampotassium, aqueous solutions thereof, or mixtures thereof, preferably sorbitol, glycerol saccharin or sodium saccharin and glycerol. Other flavouring agents may be artificial aromas such as an artificial fruit or meat aroma as for example honey, strawberry, raspberry, or beef or fish flavour, preferably honey.

The pH adjusters used may be for example sodium dihydrogen phosphate dihydrate/citric acid monohydrate buffer, glycine/HCL, K-hydrogen phthalate/HCL, citric acid/phosphate, citrate-phophate-borate/HCL or Britton-Robinson buffer, mixtures thereof or mixtures with other physiologically acceptable liquids such as glycerol or optionally aqueous solutions of sugar alcohols, preferably sodium dihydrogen phosphate dihydrate and citric acid monohydrate.

In a further embodiment the plastic container is made of PP or PET with a volume of 8 ml comprising meloxicam with a concentration of 0.5 mg/ml and sodium benzoate in a concentration of 1.5 mg/ml. More specifically said plastic container has a volume of 8 ml containing a pharmaceutical composition with a volume of 3.5 ml to 4 ml comprising meloxicam in a concentration of 0.5 mg/ml and sodium benzoate in a concentration of 1.5 mg/ml.

In a further embodiment the plastic container is made of PP or PET with a volume of 8 ml containing a pharmaceutical composition with a volume of 3.5 ml to 4 ml comprising meloxicam in a concentration of 1.5 mg/ml and sodium benzoate in a concentration of 0.8 mg/ml to 2.0 mg/ml, preferably 1.5 mg/ml.

In a further embodiment the plastic container is made of PP or PET with a volume of 8 ml containing a pharmaceutical composition with a volume of 3.5 ml to 4 ml comprising meloxicam in a concentration of 15.0 mg/ml and sodium benzoate in a concentration of 0.8 mg/ml to 2.0 mg/ml, preferably 1.5 mg/ml.

The preferred pharmaceutical composition filled into containers made of the different types of packaging has been subject to a long-term stability programme according to the conditions as described in the VICH guideline 3. The conditions used for storage were 25° C./60% r.h. (r.h.=relative humidity), 30° C./70% r.h., and 40° C. /75% r.h.

Figure 2:
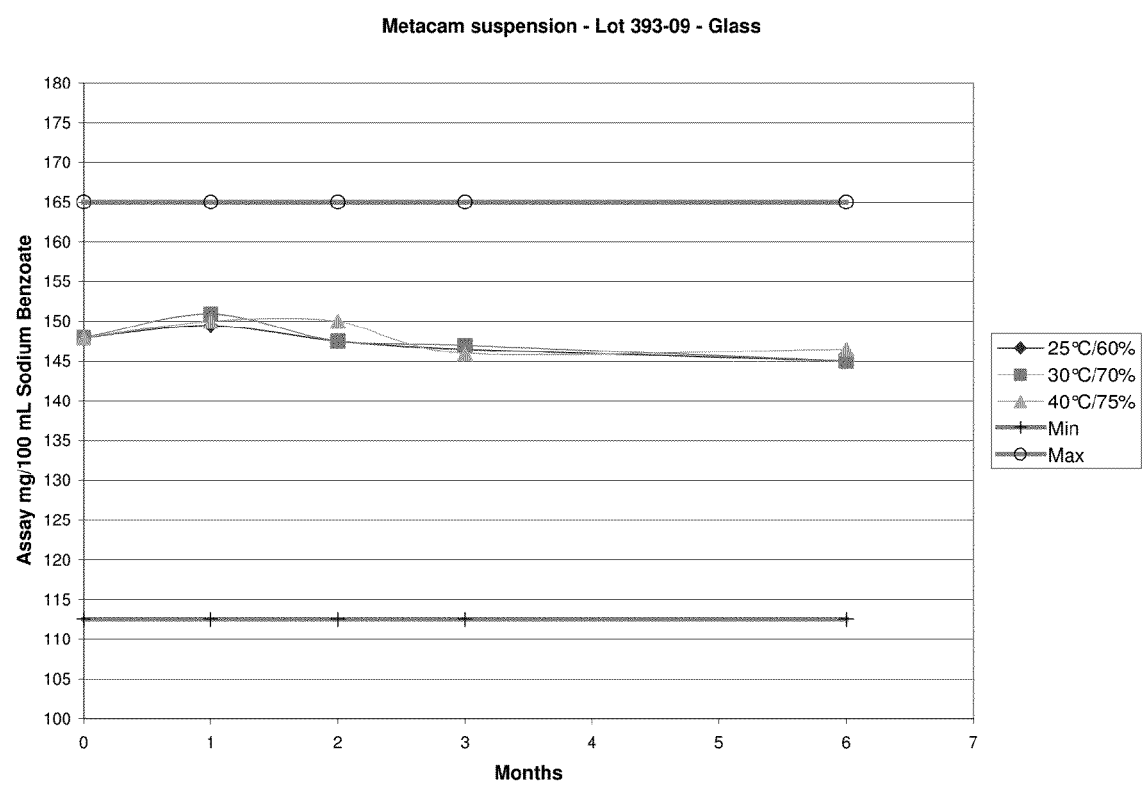
FIG. 2: Glass Bottles—Sodium Benzoate Content over Storage Time
Figure 5:
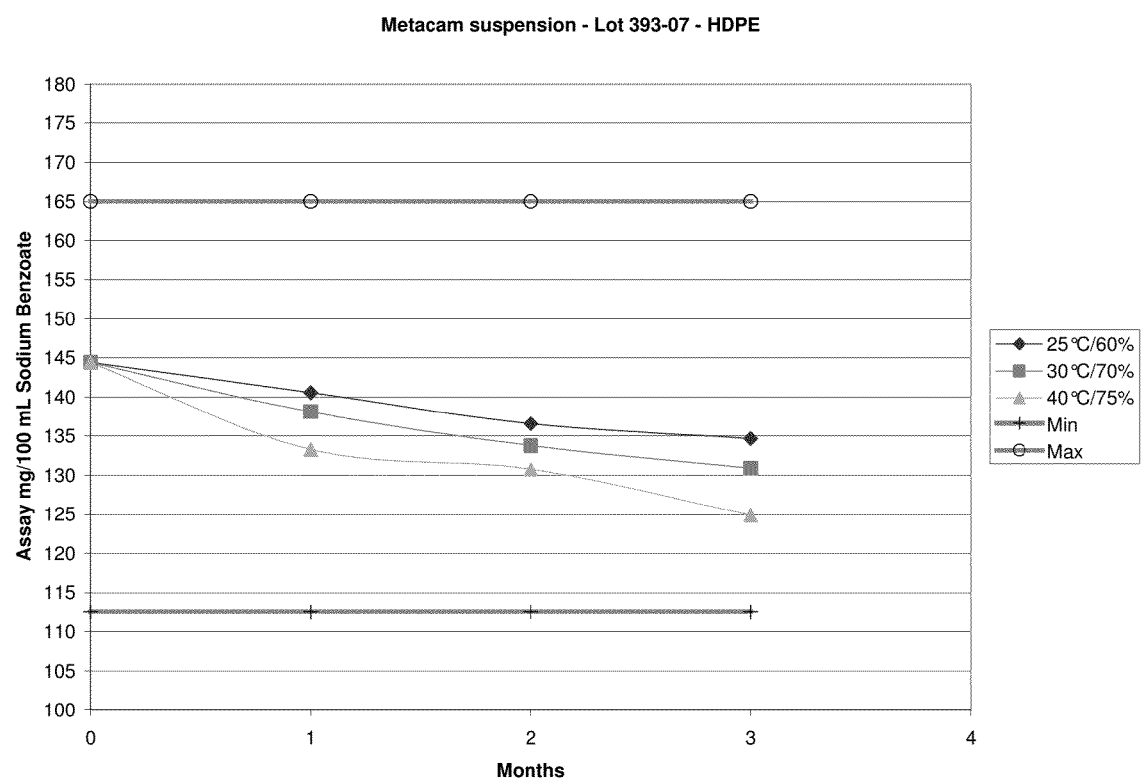
FIG. 5: HDPE Bottle—Sodium Benzoate Content over Storage Time

The stability studies of a 0.5 mg/ml suspension were carried out with 3 ml and 4 ml of the suspension being filled into 5 ml HDPE bottles. It was found that the decrease of sodium benzoate over time was surprisingly high, even directly after filling the container a significant loss of the preservative due to adsorption was observed (see FIG. 5). This has not been observed before for any of the suspensions (1.5 mg/ml or 0.5 mg/ml) or the different fill volumes. The shelf-life of the 1.5 mg/ml suspension with a 10 ml fill (in a 25 ml bottle) is for example at least 18 months. An acceptable shelf-life for commercial use of the product with a volume size for the treatment of cats for a few days (up to five days) cannot be established by using HDPE as the container material. Storage of the 0.5 mg/ml in the positive reference, namely glass bottles, shows no decrease in the sodium benzoate over time (see FIG. 2).

TABLE 1

| Ingredient | Function | 0.5 mg/ml | | 1.5 mg/ml | |
| --- | --- | --- | --- | --- | --- |
| | | g/100 ml | mg/ml | g/100 ml | mg/ml |
| Meloxicam, jet milled, BP | Active Ingredient | 0.050 | 0.50 | 0.150 | 1.50 |
| Sodium Benzoate, USP, Ph. Eur. | Preservative | 0.150 | 1.50 | 0.150 | 1.50 |
| Silica, colloidal anhydrous, USP, Ph. Eur. | Suspending Agent | 1.000 | 10.00 | 1.000 | 10.00 |
| Hydroxyethyl cellulose, USP, Ph. Eur. | Suspending Agent | 0.100 | 1.00 | 0.100 | 1.00 |
| Sorbitol Solution 70%, USP, Ph. Eur. | Flavoring Agent | 35.000 | 350.00 | 35.000 | 350.00 |
| Glycerol | Flavoring Agent | 12.750 | 127.50 | 12.750 | 127.50 |
| Saccharin Sodium Dihydrate, USP, Ph. EUR. | Flavoring Agent | 0.010 | 0.10 | 0.010 | 0.10 |
| Xylitol, USP, Ph. Eur | Flavoring Agent | 15.000 | 150.00 | 15.000 | 150.00 |
| Sodium Dihydrogen Phosphate Dihydrate, USP, Ph. Eur. | pH Adjuster | 2.000 | 20.00 | 2.000 | 20.00 |
| Citric Acid Monohydrate, USP, PH. EUR. | pH Adjuster | 0.120 | 1.20 | 0.120 | 1.20 |
| Honey Aroma (203180) | Flavoring Agent | 0.150 | 1.50 | 0.150 | 1.50 |
| Water for Injection, USP, PH. EUR. | q.s. to | q.s. to 100 ml | q.s. to 1 ml | q.s. to 100 ml | q.s. to 1 ml |

Figure 3:
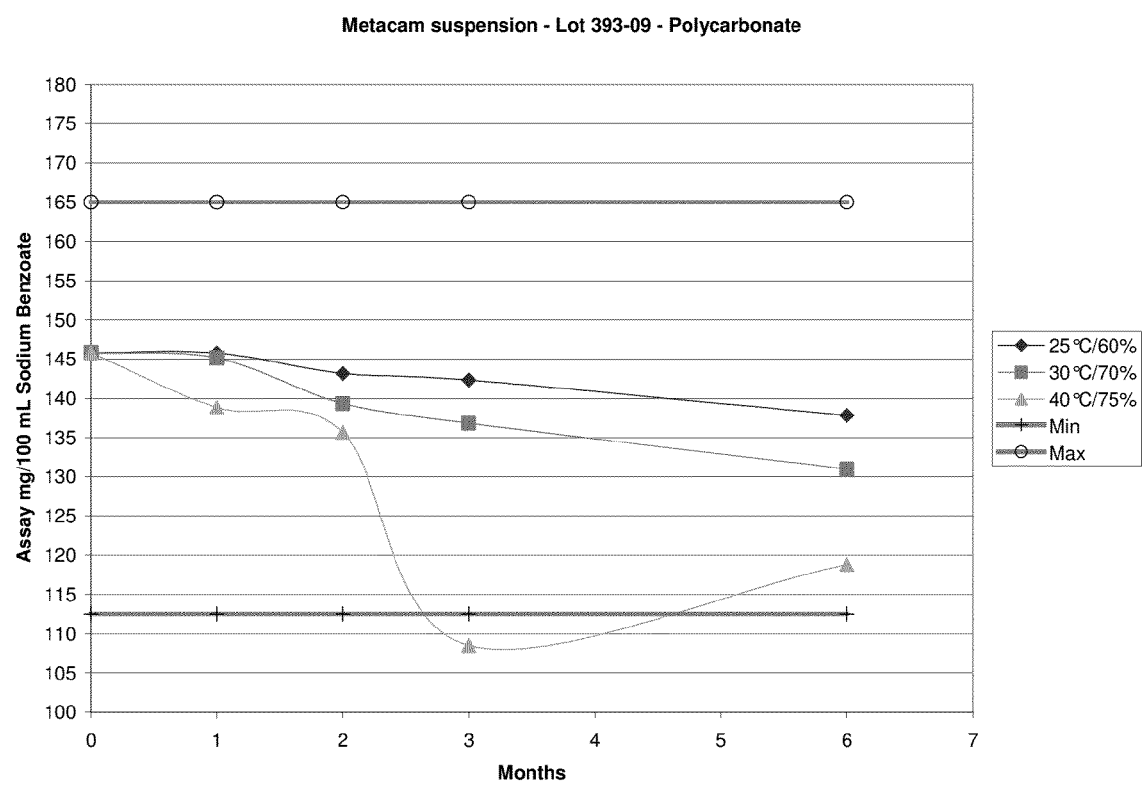
FIG. 3: PC Bottles—Sodium Benzoate Content over Storage Time
Figure 4:
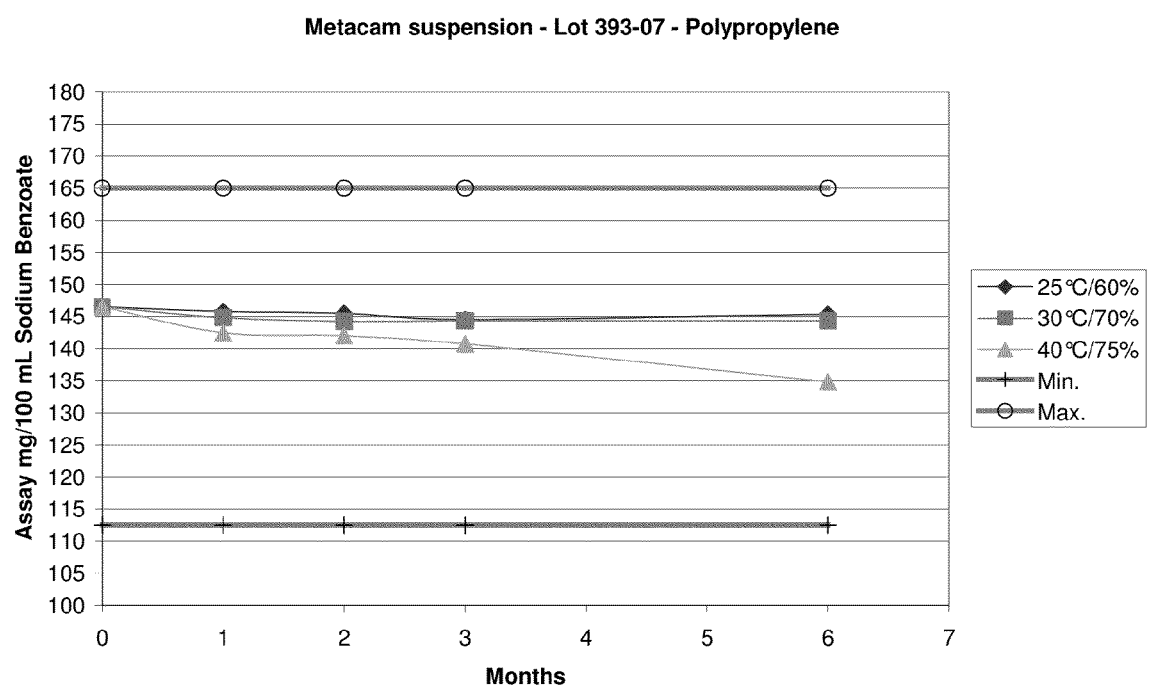
FIG. 4: PP Bottles—Sodium Benzoate Content over Storage Time
Figure 6:
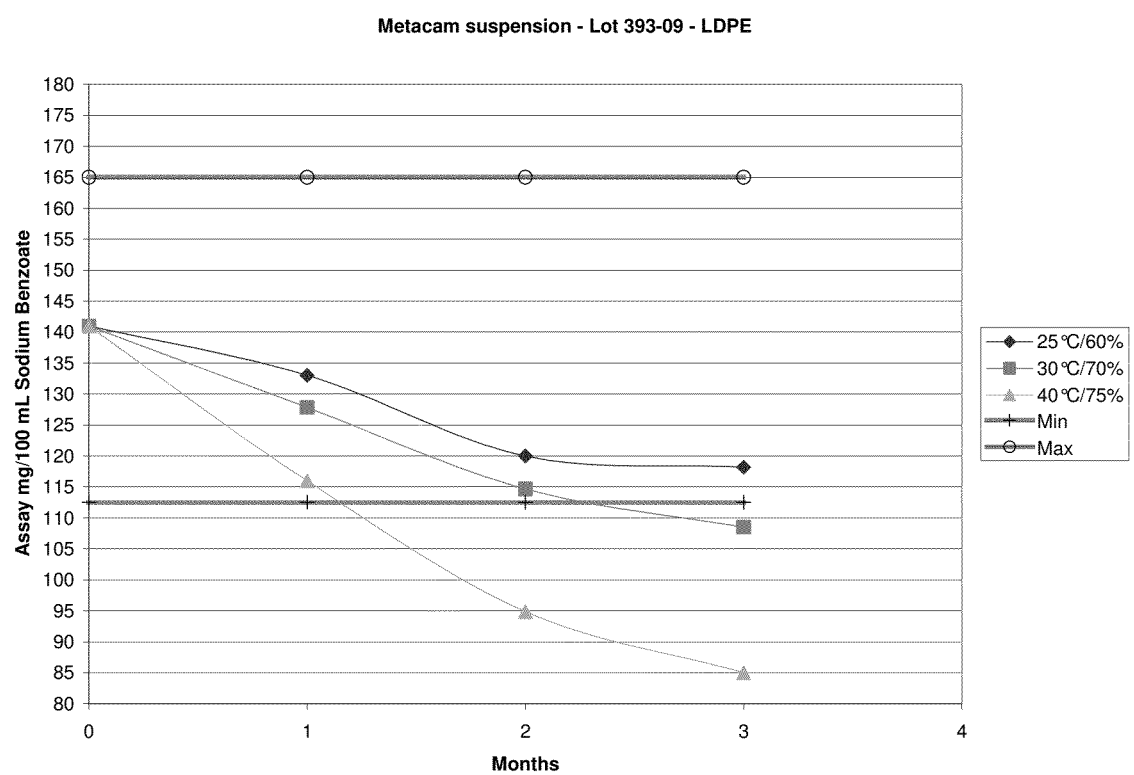
FIG. 6: LDPE Bottle—Sodium Benzoate Content over Storage Time

Surprisingly, it was found that the decrease of sodium benzoate content over a time period of 18 months or at least 18 months is significantly lower in PP bottles than in bottles made of either HDPE or LDPE (see FIG. 6). Thus, polypropylene is a suitable material for holding small volumes of oral suspensions comprising meloxicam and sodium benzoate as preservative. The suitability of PP is further shown by comparison with the unsuitable negative reference containers made of PET and PC, see FIGS. 1, 3, and 4.

Figure 7:
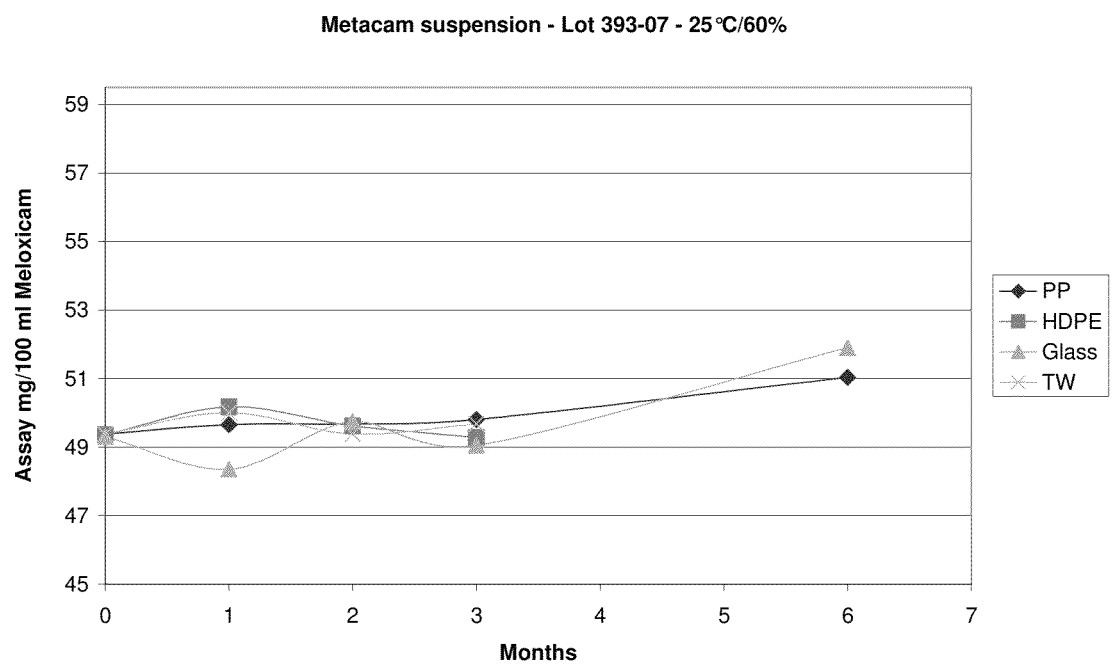
FIG. 7: Storage at 25° C./60% r.h.—Meloxicam Content for PP, HDPE and Glass Bottles (TW=Thin-walled HDPE bottles)

The meloxicam assay is very stable over time and it is demonstrated that the type of packaging material has no impact on meloxicam, see FIG. 7.

The bottle may be opaque or transparent, preferably opaque.

We claim:

1. A pharmaceutically acceptable container containing a pharmaceutical composition including sodium benzoate, the container being formed of a container material selected from one or more members of the group constisting of a homopolymer of polypropylene (PP), a copolymer of polypropylene (PP), a homopolymer of polyethylene terephthalate (PET) and a copolymer of polyethylene terephthalate (PET);
   wherein the container material does not include high-density polyethylene (HDPE), low-densisty polyethylene (LDPE), or polycarbonate (PC); and
   a loss in concentration (mg/mL) of sodium benzoate in said pharmaceutical composition due to adsorption onto said container when stored for a period of 6 months at 25° C. and a relative humidity of 60% is no more than 5%.

2. The container according to claim 1, wherein the sodium benzoate is present in the composition in a concentration range of 0.8 mg/ml to 2.0 mg/ml.

3. The container according to claim 2, wherein the composition further comprises an oxicam-type COX-inhibitor or a pharmaceutical acceptable salt thereof, the oxicam-type COX-inhibitor being selected from the group consisting of meloxicam, piroxicam, lornoxicam, tenoxicam, droxicam, and isoxicam.

4. The container according to claim 1, wherein the composition further comprises meloxicam or a pharmaceutical acceptable salt thereof.

5. The container according to claim 1 wherein the pharmaceutical composition has a volume of 2 ml to 10 ml.

6. The container according to claim 1, wherein the pharmaceutical composition is a suspension.

7. The container according to claim 1 wherein the pharmaceutical composition includes sodium benzoate in a concentration range of 0.8 mg/ml to 2.0 mg/ml, and the pharmaceutical composition further comprises meloxicam in a concentration of 0.2 mg/ml to 20 mg/ml.

8. The container according to claim 1 further comprising a closure device for storing and preserving said pharmaceutical composition.

9. The container according to claim 1, wherein:
   the container is formed of polypropylene.

10. The container according to claim 1, wherein:
    the container is formed of polyethylene terephthalate.

11. An assembly for storing and preserving a pharmaceutical composition including sodium benzoate, the assembly comprising:
    a plastic container including an opening, wherein the container consists essentially of a polymeric material and a non-polymeric component, wherein the polymeric material is selected from the group consisting of a homopolymer of polypropylene (PP), a copolymer of polypropylene (PP), a homopolymer of polyethylene terephthalate (PET) and a copolymer of polyethylene terephthalate (PET);
    a device coupled to the container proximate the opening; and
    a pharmaceutical composition stored within the container, the pharmaceutical composition comprises the sodium benzoate,
    wherein a loss in concentration (mg/mL) of sodium benzoate in said pharmaceutical composition due to adsorption onto said plastic container when stored for a period of 6 months at 25° C. and a relative humidity of 60% is no more than 5%.

12. The assembly according to claim 11, wherein the device comprises an oral dispenser for administration of the pharmaceutical composition.

13. The assembly according to claim 12, wherein the oral dispenser includes a plastic adapter and a dosing syringe.

14. The assembly according to claim 11, wherein the device is a plug-in device.

15. The assembly according to claim 14, wherein the plug-in device includes a piece that engages the container and a dosing syringe.

* * * * *